United States Patent
Huang et al.

(10) Patent No.: US 12,104,140 B2
(45) Date of Patent: Oct. 1, 2024

(54) ITACONIC ACID-BASED MULTIFUNCTIONAL SURFACTANT AND PREPARATION METHOD THEREFOR

(71) Applicant: CHANGZHOU UNIVERSITY, Jiangsu (CN)

(72) Inventors: Wenyan Huang, Changzhou (CN); Li Jiang, Changzhou (CN); Bibiao Jiang, Changzhou (CN); Qimin Jiang, Changzhou (CN); Hongjun Yang, Changzhou (CN); Xiaoqiang Xue, Changzhou (CN); Qiujie Sun, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 18/333,514

(22) Filed: Jun. 12, 2023

(65) Prior Publication Data

US 2023/0340362 A1 Oct. 26, 2023

Related U.S. Application Data

(63) Continuation of application No. 17/936,932, filed on Sep. 30, 2022, now Pat. No. 11,674,108, which is a continuation of application No. PCT/CN2020/140467, filed on Dec. 29, 2020.

(30) Foreign Application Priority Data

Mar. 31, 2020 (CN) .......................... 202010242562.2

(51) Int. Cl.
*C11D 3/30* (2006.01)
*C11D 1/00* (2006.01)

(52) U.S. Cl.
CPC .................................. *C11D 1/008* (2013.01)

(58) Field of Classification Search
CPC .................................. C11D 1/008; C11D 3/30
See application file for complete search history.

(56) References Cited

FOREIGN PATENT DOCUMENTS

| CN | 1490077 | A | 4/2004 |
|---|---|---|---|
| CN | 1966135 | A | 5/2007 |
| CN | 101249398 | A | 8/2008 |
| CN | 105441041 | A | 3/2016 |
| CN | 106496426 | A | 3/2017 |
| CN | 108221459 | A | 6/2018 |
| CN | 109206549 | A | 1/2019 |
| CN | 111302960 | A | 6/2020 |
| JP | 2010260919 | A | 11/2010 |

OTHER PUBLICATIONS

Gong, Tao et al., Synthesis of Novel Cationic Maleic Diester Polymerizable Surfactant, Journal of Hubei University ( Natural Science Edition ), 26(1): 52-56, 2004.*
Zicnanis et al., Synthesis of New Alkyl Maleates Ammonium Derivatives and Their Uses in Emulsion Polymerizetion, Colloid and Palyrnar Science, 275: 1-8, 1997.*
Qiao, Weihong et al., Synthesis and Characterization of a Novel Series of Cationic Fumaric Polymerizable Emulsifiers, J Surfact Deterg, 14: 37-41, 2011.
A. Zicnanis et al., Synthesis of New Alkyl Maleates Ammonium Derivatives and Their Uses in Emulsion Polymerization, Colloid and Polymer Science, 275: 1-8, 1997.
Zhang, Fan et al., Gemini-type Catinonic Molecules-Styrene Block Polymer Anion Conducting Membrane Prepared by in-situ Polymerization, Chinese journal of applied chemistry, 33(6): 693-700, 2016.
First Office Action in Chinese Application No. 202010242562.2 mailed on Mar. 1, 2021, 10 pages.
Decision to Grant a Patent in Chinese Application No. 202010242562.2 mailed on May 26, 2021, 2 pages.
International Search Report in PCT/CN2020/140467 mailed on Mar. 26, 2021, 7 pages.
Written Opinion in PCT/CN2020/140467 mailed on Mar. 26, 2021, 13 pages.
S. Abele et al., Cationic and Zwitterionic Polymerizable Surfactants: Quaternary Ammonium Dialkyl Maleates. 1. Synthesis and Characterization, Langmuir, 15(4): 1033-1044, 1999.

* cited by examiner

*Primary Examiner* — Charles I Boyer
(74) *Attorney, Agent, or Firm* — METIS IP LLC

(57) ABSTRACT

The present disclosure relates to a polymerizable surfactant with reducibility and a preparation method thereof. The acid anhydride is reacted with a long-chain fatty alcohol to obtain an intermediate of an anhydride monoester, and then the obtained intermediate is reacted with the hydrochloride of dimethylaminohalogenated alkane, and a polymerizable surfactant with reducibility is obtained by post-processing. The polymerizable surfactant can not only play a role as a reactive emulsifier and copolymerize with monomers to obtain a soap-free emulsion, but also form a redox initiation system with peroxide, and conduct redox emulsion polymerization at room temperature. The soap-free emulsion synthesized by the polymerizable surfactant synthesized can greatly reduce the energy consumption in production, and can carry out one-step emulsion polymerization at normal temperature or low temperature to obtain an environment-friendly emulsion with a branched structure, thereby obtaining coatings with excellent water resistance, weather resistance, and impact resistance.

14 Claims, 3 Drawing Sheets

ITACONIC ACID-BASED MULTIFUNCTIONAL SURFACTANT AND PREPARATION METHOD THEREFOR

CROSS-REFERENCE TO RELATED APPLICATIONS

This application is a continuation of U.S. patent application Ser. No. 17/936,932, filed on Sep. 30, 2022, which is a continuation of International Application No. PCT/CN2020/140467, filed on Dec. 29, 2020, which claims priority of Chinese Patent Application No. 202010242562.2 filed on Mar. 31, 2020, the contents of which are incorporated herein by reference to their entirety.

TECHNICAL FIELD

The present disclosure is a fine chemical technology field, in particular, to a polymerizable surfactant with reducibility and a preparation method thereof.

BACKGROUND

In addition to a hydrophilic group and a lipophilic group, a polymerizable surfactant also includes a reactive functional group. The reactive functional group may participate in emulsion polymerization. While playing a role of a conventional emulsifier, the reactive functional group is also bonded to the surface of polymer particles in a covalent manner to become a part of the polymer, avoiding desorption of the emulsifiers from the polymer particles or migration of the emulsifiers in an emulsion film, thereby improving the stability of the emulsion and improving the performance of the emulsion film.

Since the application of a polymerizable emulsifier for polymerization in 1956 by Bistline, a large number of polymerizable emulsifiers have been synthesized and applied to various aspects, and various materials with excellent performance have been obtained. The existing polymerizable surfactant is a series of polymerizable surfactants including different reaction groups (acrylate, styrene, maleic anhydride, etc.) and different ionic characteristics (cation, anion, non-ion, etc.). Because a soap-free emulsion system does not contain emulsifiers, the soap-free emulsion system has many excellent performance. However, due to the lack of the protective effect of the emulsifiers, the stability of the emulsion decreases and the solid content is relatively low. Therefore, developing a new type of reactive surfactant is a primary problem in soap-free emulsion polymerization.

A redox initiation system forms radical reactive species via inner sphere electron transfer (ISET), thereby initiating the polymerization of vinyl monomers. In the 1930s and 1940s, scientists of Germany, the United States, and Britain have discovered that the redox initiation system can not only shorten the induction period, but also increase the polymerization rate. Compared with the single initiator in the general thermal decomposition, the chain initiation activation energy of the redox initiation system is about 40 to 60 kJ/mol, which can reduce the polymerization temperature and even cause the polymerization to be carried out at or lower than the room temperature.

The redox initiation system initiates the polymerization quickly, and can initiate the polymerization at a lower temperature, and the obtained polymer has a high molecular weight. However, as a kind of emulsion polymerization, because a large amount of emulsifier is added, the redox initiation system also has the shortcomings of insufficient film-forming properties and mechanical properties of the emulsion.

At present, the molecular weight and solid content of environmental protection coatings are low, which cannot meet the increasingly strict regulations and construction requirements. The preparation of emulsion coatings requires a large amount of emulsifier to maintain the stability of the system, and the water resistance and mechanical properties of the coatings after emulsion film formation are poor, limiting the development and application of the environmental protection coatings.

SUMMARY

The purpose of the present invention is to introduce a tertiary amine group with reducibility into one end of acid anhydride. Because the tertiary amine has a certain hydrophilic property, the tertiary amine is used as the hydrophilic end of the polymerizable surfactant, and the other end of the acid anhydride is connected with a long carbon chain as the lipophilic end. As a result, the polymerizable surfactant with reducibility is obtained with one end being hydrophilic and the other end being lipophilic. The surfactant provided by the present disclosure uses acid anhydride, long-chain fatty alcohol, and hydrochloride of dimethylaminohaloalkane as main raw materials, and the prepared polymerizable surfactant has excellent emulsifying performance and can also be used as a reducing agent in a redox initiation reaction. One-step emulsion polymerization can be carried out at room temperature or low temperature to obtain an environmentally friendly emulsion with a branched structure, and then a coating with excellent water resistance, weather resistance, and impact resistance can be obtained.

The general structural formula of the polymerizable surfactant with reducibility provided by the present disclosure is represented as:

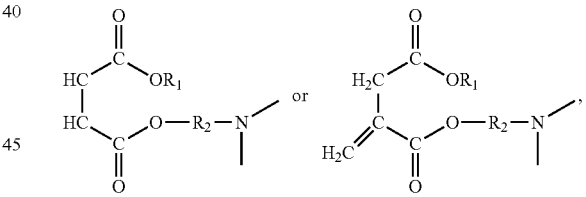

wherein a long-chain alkyl $R_1$ is $-C_{12}H_{25}$, $-C_{14}H_{29}$, or $-C_{16}H_{33}$, and a long-chain alkyl $R_2$ is $-C_2H_4-$, $-C_3H_6-$, or $-C(CH_3)CH_2-$.

The present disclosure also provides a preparation method for polymerizable surfactants with reducibility. An intermediate of anhydride monoester is obtained by reacting an anhydride with long-chain fatty alcohol. The obtained intermediate reacts with hydrochloride of dimethylaminohaloalkane. The polymerizable surfactant with reducibility is obtained through a post-treatment.

The specific operations of the preparation method of polymerizable surfactants includes:

(1) preparation of an intermediate product, including:
mixing the anhydride and the long-chain fatty alcohol; heating the mixture of the anhydride and the long-chain fatty alcohol to a molten state at 80° C.; stirring the molten mixture for 1 h; adding heptane to the molten mixture; stirring the molten mixture to form a uniform solution; stirring and cooling the solution to room temperature; placing the solution for 3 h; stirring and cooling the solution to 15° C.; placing the solution for 2 h; collecting a precipitate; recrystallizing the precipitate with heptane for 2-3 times; obtaining a solid by filtration; washing the solid with water for 2-3 times; and obtaining the intermediate monoester by freeze drying; wherein, the acidic anhydride is Malay acid anhydride or itaconic anhydride; the long-chain fatty alcohol is dodecanol, tetradecanol, or hexadecanol;

(2) preparation of the reducible polymerizable surfactant, including: dissolving the intermediate monoester of operation (1) in chloroform; adding an aqueous solution of potassium carbonate and 18-crown-6 drop by drop to the intermediate anhydride monoester chloroform solution at room temperature; stirring the chloroform solution at 50-60° C. for 0.4 h; and obtaining a reaction solution by adding a hydrochloric acid brine solution of dimethylaminohaloalkane drop by drop to the chloroform solution for reaction at 50° C. for 15-20 h; wherein, the hydrochloride salt of the dimethylaminohaloalkane is 2-dimethylaminochloroethane hydrochloride, 3-(N, N-dimethyl) amino-1-chloropropane hydrochloride or 3-dimethylamino-2-methyl-1-chloropropane hydrochloride; an amount-of-substance ratio of the anhydride and the long chain fatty alcohol in operation (1) is 1:1 to 1.1; and (3) the post treatment, including: cooling the reaction solution obtained in operation (2) to room temperature; separating each layer of the reaction solution; adding the separated chloroform solution to anhydrous sodium sulfate for drying overnight; passing the chloroform solution through an alkaline alumina column; removing the chloroform at 30-40° C. with a rotary evaporator; performing vacuum dry overnight at 30° C. with a vacuum of 2-3 kpa, wherein a resulting product is the polymerizable surfactant with reducibility.

The present disclosure has the following advantages:

1. The present disclosure uses a synthesis method to prepare a polymerization surfactant with reducibility, and the prepared surfactant has excellent emulsification performance.
2. The synthetic surfactant, along with an oxidizing agent, can form a redox initiation system, and can carry out soap-free emulsion polymerization at room temperature or even low temperature without adding additional reducing agent, which can greatly reduce the energy consumption of production.
3. The surfactant of the present invention has the properties of a monomer with reducibility, and can obtain an emulsion with a branched structure, thereby obtaining a coating with excellent water resistance, weather resistance and impact resistance.

DETAILED DESCRIPTION

The present disclosure uses the following examples to further explain the technical characteristics of the present disclosure, but the protection scope of the present disclosure is not limited to the following examples.

Embodiment 1

(1) Preparation of an intermediate. 4.90 g (0.05 mol) maleic anhydride and 10.25 g (0.055 mol) lauryl alcohol were stirred at 80° C. for 1 h at the molten state. 15 ml heptane was added to the molten mixture. The molten mixture was stirred to form a uniform solution. The solution was placed at room temperature for 3 h with stirring, and placed at 15° C. for 2 h with stirring. A precipitate was collected. The precipitate was recrystallized with heptane for 2-3 times. A solid was obtained by filtration. The solid was washed with water for 2-3 times. The intermediate of anhydride monoester was obtained by freeze drying overnight. The yield may reach 92.8%.

(2) Preparation of the polymerizable surfactant with reducibility. 11.36 g (0.04 mol) monododecyl maleate was dissolved in 100 ml chloroform. A water solution of 11.06 g (0.08 mol) potassium carbonate and 1.05 g (0.004 mol) 18-crown-6 was added dropwise to the chloroform solution at room temperature, and the mixture was stirred at 60° C. for 0.4 h. A water solution of 5.76 g (0.04 mol) 2-dimethylamino chloroethane hydrochloride (Aladdin, CAS: 4584-46-7) was added dropwise to the above water-chloroform solution, for reaction at 50° C. for 20 h.

(3) The post-treatment. The reaction solution obtained in the operation (2) was cooled to the room temperature. Each layer of the reaction solution was separated and the separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Figure 1:
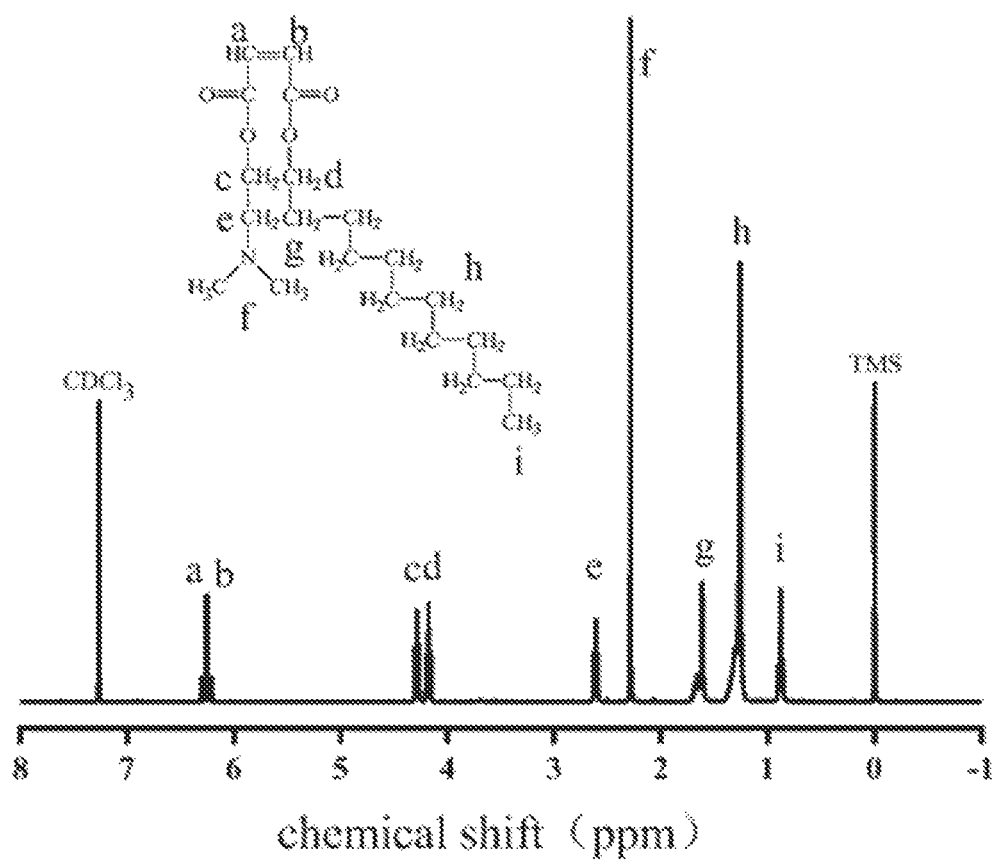
FIG. 1 is an exemplary nuclear magnetic resonance (NMR) image of 2-(dimethylamino) ethyl maleate dodecyl ester in embodiment 1.

(4) NMR analysis of the product. A small amount of the product was used for NMR analysis, and the solvent is deuterated chloroform. The peak at the chemical shift $\delta=6.26$ indicates two H atoms on the double bond, the two triple peaks at the chemical shift $\delta=4.29$ and the chemical shift $\delta=4.15$ respectively indicate —$CH_2$— connected to the ester bond, $\delta=2.60$ indicates —$CH_2$— connected to N, $\delta=2.29$ indicates two —$CH_3$ connected to N, $\delta=1.2$-1.7 indicates —$CH_2$— on the long alkyl group, $\delta=0.88$ indicates —$CH_3$ on the end of the long alkyl group. FIG. 1 is an exemplary nuclear magnetic resonance (NMR) image of 2-(dimethylamino)ethyl maleate dodecyl ester in embodiment 1.

Embodiment 2

(1) Preparation of an intermediate. 5.61 g (0.05 mol) itaconic anhydride and 9.32 g (0.05 mol) lauryl alcohol were stirred at 80° C. for 1 h at the molten state. 15 ml heptane was added to the molten mixture. The molten mixture was stirred to form a uniform solution. The solution was placed for 3 h at room temperature with stirring, and placed for 2 h at 15° C. with stirring. A precipitate was collected. The precipitate was recrystallized with heptane for 2-3 times. A solid was obtained by filtration. The solid was washed with water for 2-3 times. The intermediate monoester was obtained by freeze drying overnight. The yield may reach 93.5%.

(2) Preparation of the polymerizable surfactant with reducibility. 11.92 g (0.04 mol) itaconic acid monododecyl ester was dissolved in 100 ml chloroform. A water solution of 11.06 g (0.08 mol) potassium carbonate and 1.05 g (0.004 mol) 18-crown-6 was added dropwise to the chloroform solution at room temperature. The mixture was stirred at 50° C. for 0.4 h. A water solution of 5.76 g (0.04 mol) 2-dimethylamino chloroethane hydrochloride (Aladdin, CAS: 4584-46-7) was added dropwise to the above water-chloroform solution, for reaction at 50° C. for 20 h.

(3) The post-treatment. The reaction solution obtained in the operation (2) was cooled to the room temperature. Each layer of the reaction solution was separated. The separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Figure 2:
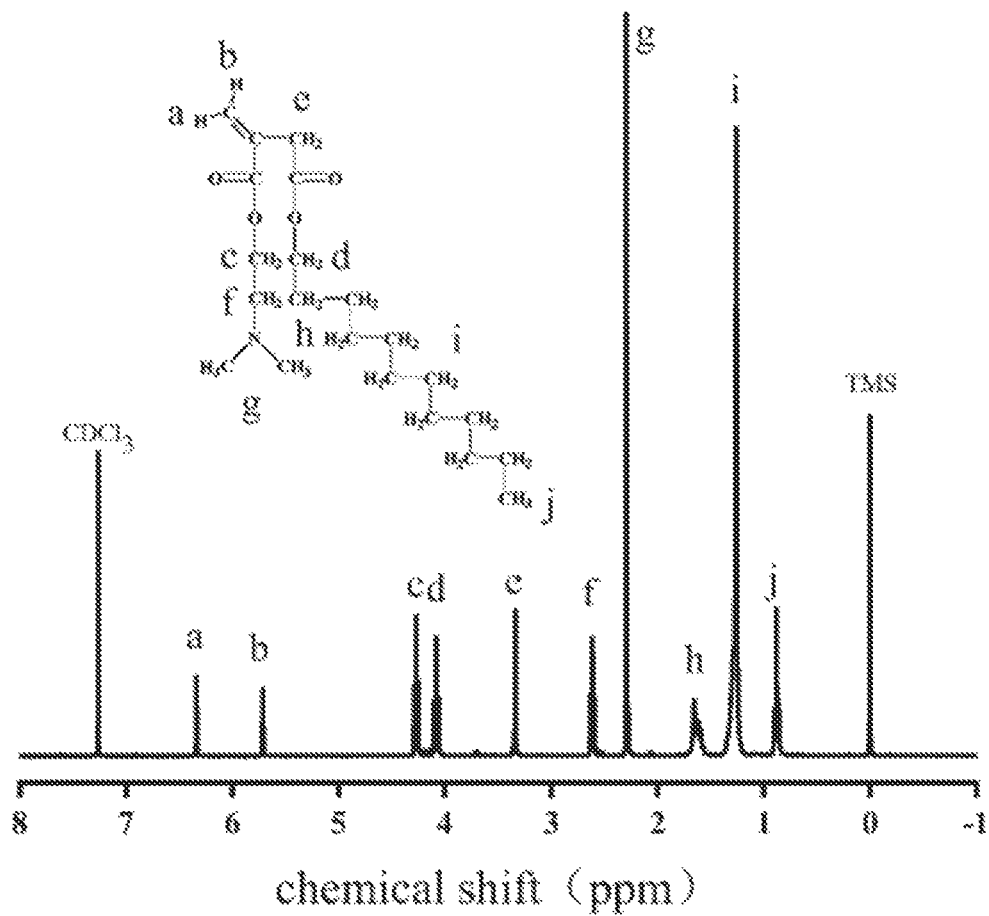
FIG. 2 is an exemplary NMR image of itaconic acid 2-(dimethylamino)ethyl dodecyl.

(4) NMR analysis of the product. A small amount of the product was used for NMR analysis, and the solvent is deuterated chloroform. The peaks at the chemical shift δ=6.34 and the chemical shift δ=5.72 indicates two H atoms on the double bond, δ=3.34 indicates —$CH_2$— connected to the carbonyl group, two triple peaks at the chemical shift δ=4.27 and the chemical shift δ=4.08 indicate —$CH_2$-connected to the ester bond. δ=2.60 indicates —$CH_2$— connected to N, δ=2.29 indicates —$CH_3$ connected to N, δ=1.2-1.7 indicates —$CH_2$— on the long-chain alkyl, δ=0.88 indicates —$CH_3$ on the end of the long alkyl group. FIG. 2 is an exemplary NMR image of itaconic acid 2-(dimethylamino)ethyl dodecyl.

Embodiment 3

(1) Preparation of an intermediate. 4.90 g (0.05 mol) maleic anhydride and 11.79 g (0.055 mol) tetradecanol were stirred at 80° C. for 1 h at the molten state. 15 ml heptane was added to the molten mixture. The molten mixture was stirred to form a uniform solution. The solution was placed for 3 h at room temperature with stirring, and placed for 2 h at 15° C. with stirring. A precipitate was collected. The precipitate was recrystallized with heptane for 2-3 times. A solid was obtained by filtration. The solid was washed with water for 2-3 times. The intermediate monoester was obtained by freeze drying overhight. The yield may reach 91.5%.

(2) Preparation of the polymerizable surfactant with reducibility. 12.48 g (0.04 mol) monotetradecyl maleate was dissolved in 100 ml chloroform. A water solution of 11.06 g (0.08 mol) potassium carbonate and 1.05 g (0.004 mol) 18-crown-6 was added dropwise to the chloroform solution at room temperature. The mixture was stirred at 60° C. for 0.4 h. A water solution of 5.76 g (0.04 mol) 2-dimethylamino chloroethane hydrochloride (Aladdin, CAS: 4584-46-7) was added dropwise to the above water-chloroform solution, for reaction at 50° C. for 20 h.

(3) The post-treatment. The reaction solution obtained in the operation (2) was cooled to the room temperature. Each layer of the reaction solution was separated. The separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Embodiment 4

(1) Preparation of an intermediate. 5.61 g (0.05 mol) itaconic anhydride and 10.72 g (0.05 mol) tetradecanol were stirred at 80° C. for 1 h at the molten state. 15 ml heptane was added to the molten mixture. The molten mixture was stirred to form a uniform solution. The solution was placed for 3 h at room temperature with stirring, and placed for 2 h at 15° C. with stirring. A precipitate was collected. The precipitate was recrystallized with heptane for 2-3 times. A solid was obtained by filtration. The solid was washed with water for 2-3 times. The intermediate monoester was obtained by freeze drying overnight. The yield may reach 92.5%.

(2) Preparation of the polymerizable surfactant with reducibility: 13.04 g (0.04 mol) itaconic acid monotetradecyl ester was dissolved in 100 ml chloroform. A water solution of 11.06 g (0.08 mol) potassium carbonate and 1.05 g (0.004 mol) 18-crown-6 was added dropwise to the chloroform solution at room temperature. The mixture was stirred at 50° C. for 0.4 h. A water solution of 5.76 g (0.04 mol) 2-dimethylamino chloroethane hydrochloride (Aladdin, CAS: 4584-46-7) was added dropwise to the above water-chloroform solution, for reaction at 50° C. for 20 h.

(3) The post-treatment. The reaction solution obtained in the operation (2) was cooled to the room temperature. Each layer of the reaction solution was separated. The separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Embodiment 5

(1) Preparation of an intermediate. 4.90 g (0.05 mol) maleic anhydride and 0.25 g (0.055 mol) lauryl alcohol were stirred at 80° C. for 1 h at the molten state. 15 ml heptane was added to the molten mixture. The molten mixture was stirred to form a uniform solution. The solution was placed for 3 h at room temperature with stirring, and placed for 2 h at 15° C. with stirring. A precipitate was collectedThe precipitate was recrystallized with heptane for 2-3 times. A solid was obtained by filtration. The solid was washed with water for 2-3 times. The intermediate monoester was obtained by freeze drying overnight. The yield may reach 91.3%.

(2) Preparation of the polymerizable surfactant with reducibility. 11.36 g (0.04 mol) monododecyl maleate was dissolved in 100 ml chloroform. A water solution of 11.06 g (0.08 mol) potassium carbonate and 1.05 g (0.004 mol) 18-crown-6 was added dropwise to the chloroform solution at room temperature. The mixture was stirred at 60° C. for 0.4 h. A water solution of 6.32 g (0.04 mol) 3-(N, N-dimethyl) amino-1-chloropropane hydrochloride (Aladdin, CAS: 5407-04-5) was added dropwise to the above water-chloroform solution, for reaction at 50° C. for 20 h.

(3) The post-treatment. The reaction solution obtained in the operation (2) was cooled to the room temperature. Each layer of the reaction solution was separated. The separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Embodiment 6

(1) Preparation of an intermediate. 4.90 g (0.05 mol) maleic anhydride and 10.25 g (0.055 mol) lauryl alcohol were stirred at 80° C. for 1 h at the molten state. 15 ml heptane was added to the molten mixture. The molten mixture was stirred to form a uniform solution. The solution was placed for 3 h at room temperature with stirring, and placed for 2 h at 15° C. with stirring. A precipitate was collected. The precipitate was recrystallized with heptane for 2-3 times. A solid was obtained by filtration. The solid was washed with water for 2-3 times. The intermediate monoester was obtained by freeze drying overnight. The yield may reach 92.8%.

(2) Preparation of the polymerizable surfactant with reducibility. 11.36 g (0.04 mol) monododecyl maleate was dissolved in 100 ml chloroform. A water solution of 11.06 g (0.08 mol) potassium carbonate and 1.05 g (0.004 mol) 18-crown-6 was added dropwise to the chloroform solution. The mixture was stirred at 60° C. for 0.4 h. A water solution of 6.88 g (0.04 mol) 3-dimethylamino-2-methyl-1-chloropropane hydrochloride (Aladdin, CAS: 4261-67-0) was added dropwise to the above water-chloroform solution, for reaction at 50° C. for 20 h.

(3) The post-treatment. The reaction solution obtained in the operation (2) was cooled to the room temperature. Each layer of the reaction solution was separated. The separated chloroform solution was added to anhydrous sodium sulfate for drying overnight. The chloroform solution passed through an alkaline alumina column. The chloroform was removed at 30-40° C. with a rotary evaporator. Vacuum dry was performed overnight at 30° C. with a vacuum of 2-3 kpa, wherein a resulting product is the polymerizable surfactant with reducibility.

Embodiment 7

Figure 3:
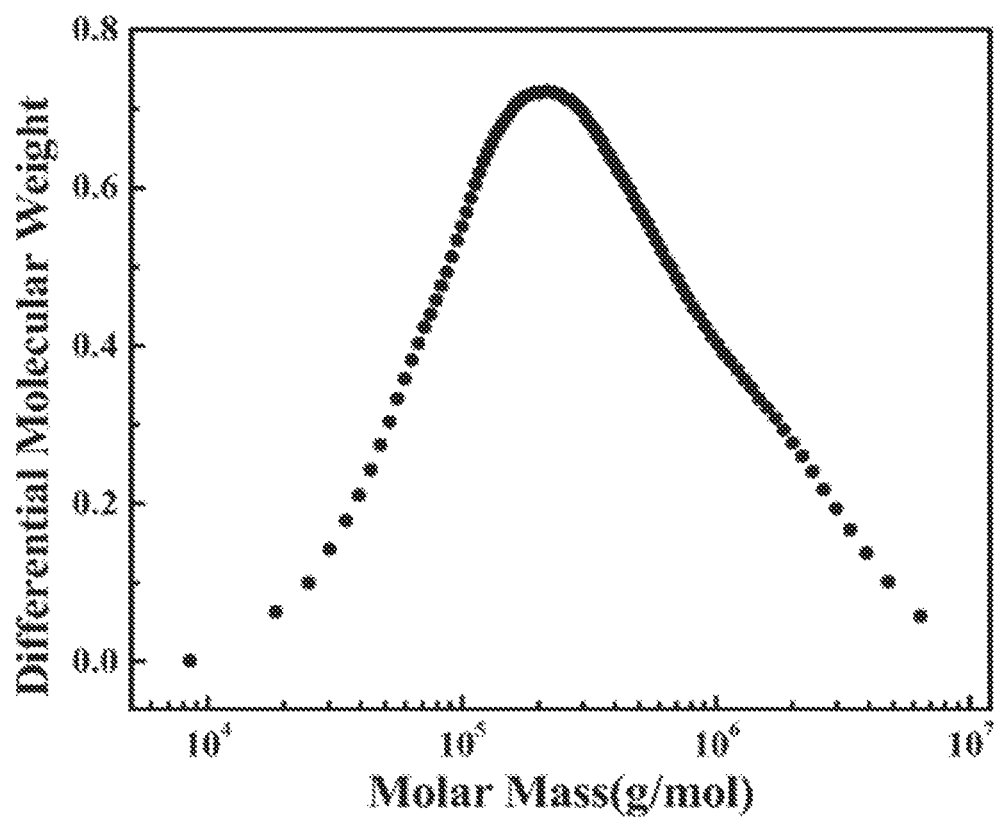
FIG. 3 is an exemplary molecular weight distribution curve of a branched polymer obtained in the embodiment 7.

Styrene (5.01 g, 0.0480 mol) was added to a reaction bottle including 2-(dimethylamino)ethyl maleate lauryl ester (0.3550 g, 0.0010 mol), sodium bicarbonate (0.15 g, 3 wt % styrene), potassium sulfate (0.1344 g, 0.0005 mol), and water (20.07 g, 400 wt % styrene). The solution was stirred evenly. After vacuuming and deoxygenating, the solution was placed at 25° C. for 8 hours to obtain a stable emulsion. The conversion rate of the styrene was 91.07%. The polymer was analyzed by triple-detection gel permeation chromatography and the results were as follows: M n.SEC=418000 g/mol, M w.SEC=2560000 g/mol, PDI=6.1.Mark-Houwink, α=0.6756, an average branching factor g'=0.66. The molecular weight distribution curve of the obtained polymer is in FIG. 3.

Embodiment 8

Styrene (5.0005 g, 0.0480 mol) was added to a reaction bottle including itaconic acid 2-(dimethylamino)ethyl dodecyl (0.3552 g, 0.0010 mol), sodium bicarbonate (0.15 g, 3 wt % styrene), potassium sulfate (0.1340 g, 0.0005 mol), and water (20.07 g, 400 wt % styrene). The solution was stirred evenly. After vacuuming and deoxygenating, the solution was placed at 25° C. for 8 hours to obtain a stable emulsion. The conversion rate of the styrene was 98.05%. The polymer was analyzed by triple-detection gel permeation chromatography and the results were as follows: M n.SEC=263000 g/mol, M w.SEC=2970000 g/mol, PDI=11.3.Mark-Houwink, α=0.5992, an average branching factor g'=0.52.

Embodiment 9

Styrene (5.00 g, 0.0480 mol) was added to a reaction bottle including 3-(dimethylamino)propyl maleate lauryl ester (0.3555 g, 0.0010 mol), sodium bicarbonate (0.15 g, 3 wt % styrene), potassium sulfate (0.2619 g, 0.0010 mol), and water (20.07 g, 400 wt % styrene). The solution was stirred evenly. After vacuuming and deoxygenating, the solution was placed at 25° C. for 8 hours to obtain a stable emulsion. The conversion rate of the styrene was 90.25%. The polymer was analyzed by triple-detection gel permeation chromatography and the results were as follows: M n.SEC=530000 g/mol, M w.SEC=6520000 g/mol, PDI=12.3.Mark-Houwink, α=0.889, an average branching factor g'=0.50.

Comparative Example 1

Styrene (5.0006 g, 0.0480 mol) and N,N-dimethylaminoethyl methacrylate (0.1510 g, 0.0010 mol) was added to a reaction bottle including sodium bicarbonate (0.1500 g, 3 wt % styrene), potassium persulfate (0.2596 g, 0.0010 mol), and water (20.0020 g, 400 wt % styrene). The solution was stirred evenly. After vacuuming and deoxygenating, the solution was placed at 25° C. There is no reaction in the system.

What is claimed is:

1. A method for preparing a polymerizable surfactant with reducibility, wherein a general structural formula of the polymerizable surfactant with reducibility is represented as:

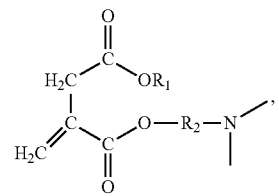

wherein a long-chain alkyl $R_1$ is $-C_{12}H_{25}$ or $-C_{14}H_{29}$, and a long-chain alkyl $R_2$ is $-C_2H_4-$ or $-C_3H_6-$;

the method comprising:

performing a reaction based on an anhydride, long-chain fatty alcohol, and hydrochloride of dimethylaminohaloalkane; and obtaining the polymerizable surfactant with reducibility through a post-treatment performed on a reaction solution obtained based on the reaction.

2. The method of claim 1, wherein an amount-of-substance ratio of the anhydride and the long chain fatty alcohol is 1:1 to 1.1.

3. The method of claim 1, wherein the anhydride is itaconic anhydride.

4. The method of claim 1, wherein the long-chain fatty alcohol is dodecanol or tetradecanol.

5. The method of claim 1, wherein the hydrochloride of dimethylaminohaloalkane is 2-dimethylaminochloroethane hydrochloride, 3-(N, N-dimethyl) amino-1-chloropropane hydrochloride, or 3-dimethylamino-2-methyl-1-chloropropane hydrochloride.

6. The method of claim 1, wherein performing the reaction based on the anhydride, the long-chain fatty alcohol, and the hydrochloride of dimethylaminohaloalkane includes:

obtaining an intermediate of anhydride monoester by reacting the anhydride with the long-chain fatty alcohol; and obtaining the reaction solution by reacting the obtained intermediate with the hydrochloride of dimethylaminohaloalkane.

7. The method of claim 6, wherein an amount-of-substance ratio of the hydrochloride of dimethylaminohaloalkane and the intermediate of anhydride monoester is 1 to 1.1:1.

8. The method of claim 6, wherein obtaining the intermediate of anhydride monoester by reacting the anhydride with the long-chain fatty alcohol includes:

mixing the anhydride and the long-chain fatty alcohol;

heating the mixture of the anhydride and the long-chain fatty alcohol to a molten state;

adding heptane to the molten mixture to form a solution;

cooling the solution to obtain a precipitate; and obtaining the intermediate of anhydride monoester by recrystallization, filtration, washing, and freeze drying with respect to the precipitate.

9. The method of claim 6, wherein obtaining the reaction solution by reacting the obtained intermediate with the hydrochloride of dimethylaminohaloalkane includes:

dissolving the intermediate of anhydride monoester in chloroform;

adding an aqueous solution of potassium carbonate and 18-crown-6 to the intermediate anhydride monoester chloroform solution; and obtaining the reaction solution by adding an aqueous solution of the hydrochloride of dimethylaminohaloalkane to the intermediate anhydride monoester chloroform solution for reaction.

10. The method of claim 9, wherein an amount-of-substance ratio of the potassium carbonate, the 18-crown-6, and the intermediate of anhydride monoester is 2:0.1:1.

11. The method of claim 6, wherein obtaining the intermediate of anhydride monoester by reacting the anhydride with the long-chain fatty alcohol includes:

mixing the anhydride and the long-chain fatty alcohol;

heating the mixture of the anhydride and the long-chain fatty alcohol to a molten state at 80° C.;

stirring the molten mixture for 1 h;

adding heptane to the molten mixture;

stirring the molten mixture to form a uniform solution;

stirring and cooling the solution to room temperature;

placing the solution for 3 h;

stirring and cooling the solution to 15° C.;

placing the solution for 2 h;

collecting a precipitate;

recrystallizing the precipitate with heptane for 2-3 times;

obtaining a solid by filtration;

washing the solid with water for 2-3 times; and obtaining the intermediate of anhydride monoester by freeze drying.

12. The method of claim 6, wherein obtaining the reaction solution by reacting the obtained intermediate with the hydrochloride of dimethylaminohaloalkane includes:

dissolving the intermediate of anhydride monoester in chloroform;

adding an aqueous solution of potassium carbonate and 18-crown-6 drop by drop to the intermediate anhydride monoester chloroform solution at room temperature;

stirring the chloroform solution at 50-60° C. for 0.4 h; and obtaining the reaction solution by adding an aqueous solution of the hydrochloric of dimethylaminohaloalkane drop by drop to the intermediate anhydride monoester chloroform solution for reaction at 50° C. for 15-20 h.

13. The method of claim 1, wherein obtaining the polymerizable surfactant with reducibility through the post-treatment performed on the reaction solution obtained based on the reaction includes:

cooling the reaction solution to room temperature;

separating each layer of the reaction solution;

adding separated chloroform solution to anhydrous sodium sulfate for drying;

passing the chloroform solution through an alkaline alumina column;

removing the chloroform; and performing vacuum dry, wherein a resulting product is the polymerizable surfactant with reducibility.

14. The method of claim 1, wherein obtaining the polymerizable surfactant with reducibility through the post-treatment performed on the reaction solution obtained based on the reaction includes:

cooling the reaction solution to room temperature;

separating each layer of the reaction solution;

adding separated chloroform solution to anhydrous sodium sulfate for drying overnight;

passing the chloroform solution through an alkaline alumina column;

removing the chloroform at 30-40° C. with a rotary evaporator;

performing vacuum dry overnight at 30° C. with a vacuum of 2-3 kpa, wherein a resulting product is the polymerizable surfactant with reducibility.

* * * * *